United States Patent [19]

Lamb, Jr.

[11] Patent Number: 4,573,987
[45] Date of Patent: Mar. 4, 1986

[54] REUSABLE MULTI-LAYERED DIAPER WITH WICKING ACTION

[75] Inventor: Kenneth A. Lamb, Jr., Miami, Fla.

[73] Assignee: KW Marketing Incorporated, Miami Lakes, Fla.

[21] Appl. No.: 716,683

[22] Filed: Mar. 27, 1985

[51] Int. Cl.$^4$ .............................................. A61F 13/16
[52] U.S. Cl. ..................................................... 604/378
[58] Field of Search ............... 604/378, 396, 385, 358, 604/394, 374, 370, 371, 372, 377

[56] References Cited

U.S. PATENT DOCUMENTS

| | | | |
|---|---|---|---|
| 2,770,237 | 11/1956 | Starr | 604/394 |
| 2,829,647 | 4/1958 | Dexter | |
| 3,237,625 | 3/1966 | Johnson | 604/396 |
| 3,530,859 | 9/1970 | Heimowitz | |
| 3,749,095 | 7/1973 | Toyama | 604/396 |
| 3,828,785 | 8/1974 | Gamm et al. | 604/394 |
| 4,196,733 | 4/1980 | Elias-Geisseler | |
| 4,244,367 | 1/1981 | Rollenhagen | 604/396 |
| 4,411,660 | 10/1983 | Dawn et al. | 604/378 |

Primary Examiner—John D. Yasko
Attorney, Agent, or Firm—Oltman and Flynn

[57] ABSTRACT

A multi-layer diaper for use in contact with skin to absorb body wastes. The description of the multi-layers as follows: layer 1 an interior shell 100% cotton liner soft absorbing nonallergenic next to the body; layer 2 100% synthetic nonwoven bonded monofilament synthetic material allowing moisture to pass through to lower layers, carrying wetness away from body in a wicking action; layer 3 100% cotton wetting pad for maximum additional absorbency with minimum bulk; layer 4 terry cloth cotton/polyester blend providing extra absorbency and layer 5 terry cloth cotton/polyester blend extra absorbency giving finished look to exterior of diaper.

3 Claims, 3 Drawing Figures

REUSABLE MULTI-LAYERED DIAPER WITH WICKING ACTION

BACKGROUND OF THE INVENTION

The present invention relates to reusable absorbent baby diapers. The primary purpose of the invention is to collect body wastes such as urine and fecal matter until the diaper is changed. The primary object sought is to provide maximum comfort and health safety for the baby.

The greatly increased use of synthetic disposable products over the past twenty years including baby diapers and female napkins has brought to scientists' attention the correlation of bacterial diseases and human waste materials trapped against the body in an air locked fashion, thus creating a greenhouse effect. Additionally, the use of modern synthetic materials directly against human skin has led to the discovery of high amounts of perviously unencountered allergic reactions ranging from diaper rash to more serious medical problems.

Disposable products are also posing public health hazards. Intestinal and polio viruses can survive for weeks in disposable diapers contaminating landfills and water supplies. Highly toxic human waste materials are usually processed using modern sewer processing and chemical treatment techniques. Disposable diapers bypass these entire waste treatment processes. The actual threat to sanitation workers and the public at large is still unknown.

Mothers today as well as professional baby care centers are returning to a "good old days" approach for diapers. Natural 100% cotton is one of the least allergenic materials known to man. Coincidentally, it is also one of the most moisture absorbent materials known to man. Additionally it is a highly gas pervious or breathable material. Finally, it offers a minimum bulk for its high moisture absorbency.

The problem with simply using a one layer cotton diaper is that all the moisture stays evenly distributed throughout the diaper. Thus a high amount of urine remains in direct contact with the baby's skin until the diaper is changed. This can cause diaper rash.

An additional problem with a simple all cotton one layer diaper is wrinkling after washing. Time is needed to fold the diapers for maximum comfort and storability.

The traditional rectangular shape of a diaper requires either folding to properly fit babies as they grow or purchasing various sized diapers over the approximate thirty month period of diaper use.

PRIOR ART

U.S. Pat. No. 3,237,625 to Johnson discloses a baby training panty. A wicking layer of synthetic material is used to draw the moisture away from the body. It is the object of this invention to provide a plurality of layers of moisture absorbent material as second and subsequent layers to hold the moisture away from the skin of the wearer. The synthetic fiber is the first layer in direct contact with the skin. The invention is related to postdiaper use by an infant in toilet training. The size of the panty is fixed for slip on-use.

U.S. Pat. No. 3,530,859 to Heimowitz discloses a multi-layer terrycloth and cotton diaper shaped like a panty with an expansible waistband and snaps. The inner layers of terrycloth rest directly on the infant's skin and are designed to absorb moisture and permit air and vapor passage through the diaper. An outer less absorbent fabric helps prevent the passage of moisture out onto other garments. A crotch pocket design aids in containing solids.

U.S. Pat. No. 4,196,733 to Elias-Geisseler discloses a multi-layered reusable diaper comprising various natural or man made fibers. To use, the garment is folded along a center line. There exists a waterproof covering ply to eliminate or reduce the need for outer rubber panties. The construction is designed to eliminate the discomfort created by lumps and folds which traditional "double diapering" causes.

None of the art discussed above teaches a multilayered diaper using a non-allergenic 100% cotton layer in contact with the skin followed by a synthetic nonabsorbent monofilament layer made of polyester or an equivalent, which layer provides a wicking action to draw and hold moisture away from the skin and absorb it in multiple layers of cotton and terrycloth. The combination of the layers is substantially air vapor porous or breathable, providing maximum health protection for the skin. Additionally the unique contoured and fitted shape with overlapping flaps allows one size to fit all infants while provding maximum comfort. This invention in essence provides a wicking diaper out of cloth, allowing maximum health safety and comfort for an infant, all at an overall lower cost than disposable diapers.

SUMMARY OF THE INVENTION

The primary object of the present invention is to provide a multi-layer reusable diaper offering the maximum health features of:

First, using a non-allergenic 100% cotton fabric against the baby's skin;

Second, to wick or draw the moisture away from baby's body and hold it away in multiple layers of highly absorbent cotton and terrycloth; and Third, to provide that the total combination of layers is substantially air vapor porous and breathable.

Another object of the present invention is to provide a design and contoured shape allowing a single size to fit all infants. The overlapping flaps, matching concave curves and thin lower strip allow three distinct folding methods to cover any sized infant with a proper snug, leg contoured, high back and below the navel fit. The overlapping flaps allow easy single pin fastening for smaller infants.

These objects and others will become apparent from the drawings, the description given herein and the appended claims.

In one embodiment, the present invention provides a multilayer diaper offering maximum health protection with an ideal balance of comfort, cost and absorbency utilizing a five layer construction. The layers are described as follows:

Layer 1:
  Interior shell 100% cotton liner soft absorbing nonallergenic next to the body.

Layer 2:
  100% synthetic nonwoven bonded monofilament material allows moisture to pass through to lower layers. It carries wetness away from body in a wicking action.

Layer 3:

100% cotton wetting pad for maximum additional absorbency with minimum bulk.

Layer 4:

Terry cloth cotton/polyester blend provides extra absorbency.

Layer 5:

Terry cloth cotton/polyester blend extra absorbency gives finished look to exterior of diaper.

Note: Layers are described from inside layer out and layers 2, 3, 4 make up wetting pad.

The materials are matched in strength to withstand approximately the same number of washing and drying machine cycles before disintegrating. The use of polyester and cotton fabrics greatly increases the diaper's useful life.

The contour is the proven one size fits all Fred Dexter B-29 diaper, U.S. Pat. No. 2,829,647, expired. The double matching concave sides allow leg contouring fits for all sizes. The thin lower strip opposite the overlapping flaps allows ease of folding for fitting the smallest infant. No folding is required before use.

The combination polyester and cotton terrycloth layers eliminates wrinkles. The outermost terrycloth layer gives a panty like dressed appearance. The material is appropriate for a wet pad in a crib play area environment.

In another embodiment all layers except the second from the skin are made of terrycloth. The second layer remains a polyester or equivalent. This embodiment is less expensive to produce while sacrificing some absorbency, providing a less smooth textured surface on the baby's skin for use on less sensitive skin and adding slightly more bulk to the diaper.

In another embodiment additional layers of either cotton and/or terrycloth are added to the first five of embodiments one and two to provide a "double diaper" in a single diaper. Appropriate use could include overnight use or trips where frequent changing is not feasible or for especially wet infants.

Other objects of this invention will appear from the following description and appended claims, reference being had to the accompanying drawings forming a part of this specification wherein like reference characters designate corresponding parts in the several views.

Before explaining the disclosed embodiments of the present invention in detail, it is to be understood that the invention is not limited in its application to the details of the particular arrangements shown, since the invention is capable of other embodiments. Also, the terminology used herein is for the purpose of description and not of limitation.

DESCRIPTION OF THE PREFERRED EMBODIMENTS

Figure 1:
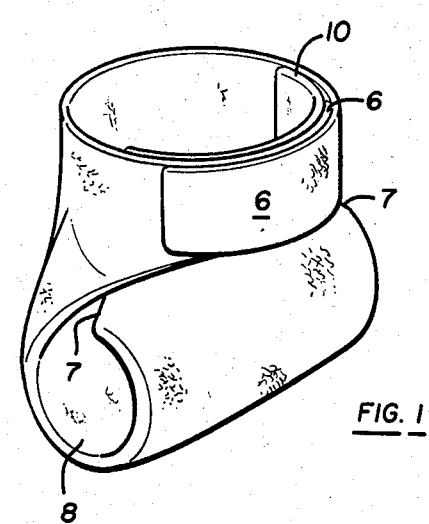
FIG. 1 is a perspective view of the folded diaper displaying the overlapped flaps and leg contoured curves.

Referring first to FIG. 1, the time proven Dexter design as noted above is illustrated in its folded position on an infant. The lower edge 10 is shown folded up approximately even with the flaps 6. The flaps overlap allowing a single safety pin to fasten the diaper firmly around the infant. The concave curves 7 and 8 provide a circular leg contouring fit without bumps and folds.

Figure 3:
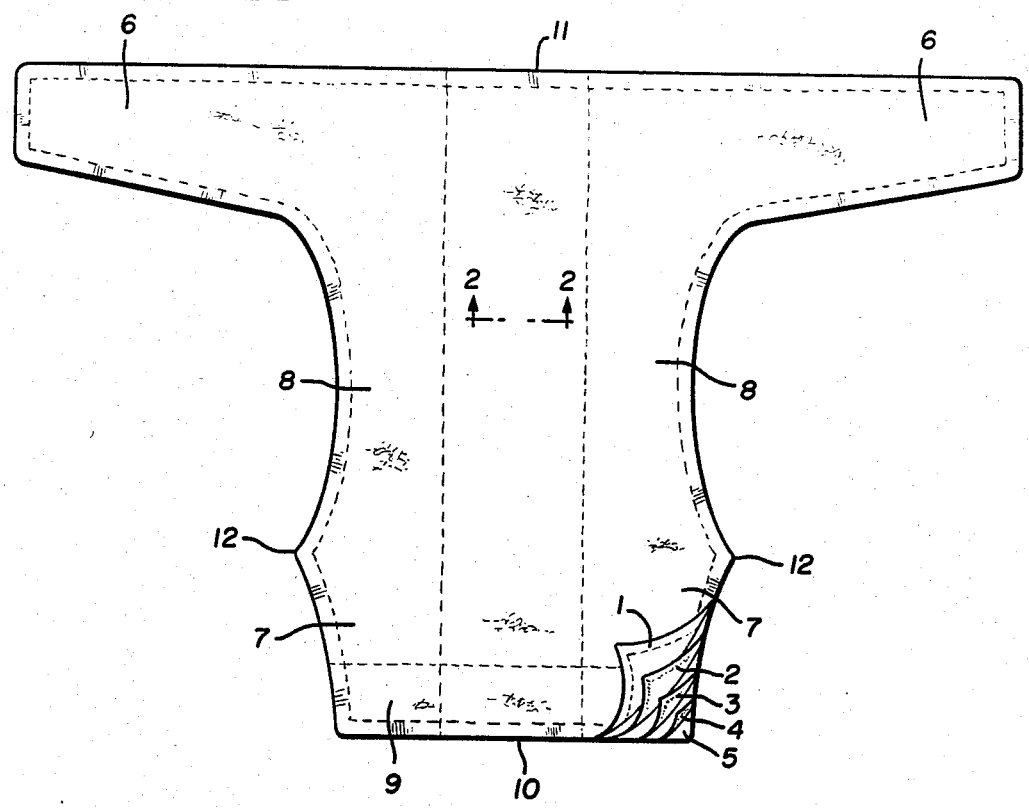
FIG. 3 shows the unfolded basic shape of the diaper.

FIG. 3 depicts the diaper in its flat position. The dimensions are substantially the same as the expired Dexter U.S. Pat. No. 2,829,647. The length from flap to flap is approximately twenty and one half inches. The length from the top 11 to the bottom 10 is approximately thirteen inches. The length across the concave curves junction at tips 12 is approximately nine inches. The tips 12 occur approximately three and one half inches above the bottom edge 10. The thinner easily folded bottom edge at 9 is approximately one and one half inches wide running across the bottom edge 10.

Figure 2:
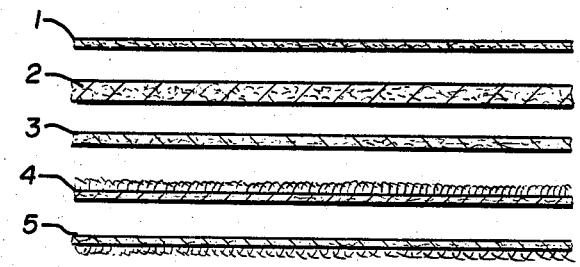
FIG. 2 is an elevational fragmentary sectional view of the five layers of the preferred embodiment.

FIG. 2 depicts the five layers of the preferred embodiment as follows:

Layer 1:

Interior shell 100% cottom liner soft absorbing nonallergenic next to the body.

Layer 2:

100% synthetic nonwoven bonded monofilament material allows moisture to pass through to lower layers. It carries wetness away from body in a wicking action. This wicking material is comprised of 100% polyester or cellulose triacetate, polyamide, polyvinyl chloride, polypropylene, acrylic, or modacrylic or equivalent hydrophobic substance. Its bonded strength and thickness must enable it to withstand as many washing and drying machine cycles as any other layer of the diaper. This layer functions as a semi-impervious barrier for wicking moisture away from the skin into the more absorbent third, fourth, fifth (or more) layers.

Layer 3:

100% cotton wetting pad for maximum additional absorbency with minimum bulk.

Layer 4:

Terry cloth cotton/polyester blend provides extra absorbency.

Layer 5:

Terry cloth cotton/polyester blend extra absorbency gives finished look to exterior of diaper.

It will be understood that the alternative embodiments utilizing a less expensive all terrycloth construction for layers 1, 3, 4 and 5 and/or further layers of terrycloth and/or cotton to provide a "double diaper" effect can result in numerous embodiments.

I claim:

1. A multi-layer reusable, washable diaper for use in contact with the skin comprising:
   a 100% natural cotton first layer for contacting the skin;
   a hydrophobic contiguous second layer having a synthetic bonded monofilament construction providing a wicking action for drawing moisture away from the skin;
   a highly absorbent cotton third layer;
   a highly absorbent combination cotton and synthetic bonded monofilament terrycloth fourth layer;
   a highly absorbent combination cotton and synthetic bonded monofilament terrycloth outer fifth layer;
   said diaper providing a breathable air vapor porous characteristic at normal atmospheric pressure throughout the combination of all layers of the diaper;
   all layers of said diaper constructed with substantially the same resistance to machine washing and drying.

2. The diaper of claim 1 comprising additional highly absorbent cotton and/or cotton and synthetic bonded monofilament terrycloth layers to achieve a double diaper effect in a single diaper.

3. The diaper of claim 1, comprising polyester as the synthetic bonded monofilament material.

* * * * *